(12) United States Patent
Panton et al.

(10) Patent No.: US 12,097,520 B2
(45) Date of Patent: Sep. 24, 2024

(54) WIRELESS ULTRA SONIC DIFFUSER

(71) Applicant: Vitruvi Corporation, Vancouver (CA)

(72) Inventors: Sean Panton, Vancouver BC (CA);
Sara Panton, Vancouver (CA);
Harpeet Gill, Surrey (CA)

(73) Assignee: Vitruvi Corporation, Vancouver (CA)

( * ) Notice: Subject to any disclaimer, the term of this patent is extended or adjusted under 35 U.S.C. 154(b) by 884 days.

(21) Appl. No.: 17/070,811

(22) Filed: Oct. 14, 2020

(65) Prior Publication Data

US 2022/0111411 A1    Apr. 14, 2022

(51) Int. Cl.
| B05B 17/06 | (2006.01) |
| A61L 9/14 | (2006.01) |
| H01M 10/0525 | (2010.01) |

(52) U.S. Cl.
CPC ............ B05B 17/0615 (2013.01); *A61L 9/14* (2013.01); *H01M 10/0525* (2013.01); *A61L 2202/14* (2013.01); *A61L 2209/15* (2013.01)

(58) Field of Classification Search
CPC .... A61L 2202/14; A61L 2202/15; A61L 9/14; A61L 2209/132; A61L 2209/12; A61L 2209/11; A61L 2209/134; A61L 9/12; A61L 9/122; A61L 9/032; B05B 17/0615; B05B 14/00; B05B 14/30; B05B 14/44; B05B 17/0607

See application file for complete search history.

(56) References Cited

U.S. PATENT DOCUMENTS

| 5,221,025 | A | * | 6/1993 | Privas ................. B05B 11/1052 |
| | | | | 128/200.14 |
| 9,914,145 | B2 | * | 3/2018 | Osborn .................... F21V 29/67 |
| 10,112,203 | B2 | * | 10/2018 | Kubicek ............... B05B 7/0012 |
| 2008/0223953 | A1 | * | 9/2008 | Tomono ............... A61M 11/005 |
| | | | | 128/200.16 |
| 2017/0112196 | A1 | * | 4/2017 | Sur ...................... H05B 1/0244 |
| 2019/0015539 | A1 | * | 1/2019 | Sullivan ................. A61L 9/122 |
| 2019/0224702 | A1 | * | 7/2019 | Pitcher ..................... A61L 9/12 |

* cited by examiner

*Primary Examiner* — Christopher R Dandridge

(74) *Attorney, Agent, or Firm* — Merchant & Gould P.C.

(57) ABSTRACT

A battery-operated ultrasonic diffuser includes a rechargeable lithium-ion battery and a liquid management system that allows a user to safely move the diffuser when it is full.

13 Claims, 18 Drawing Sheets

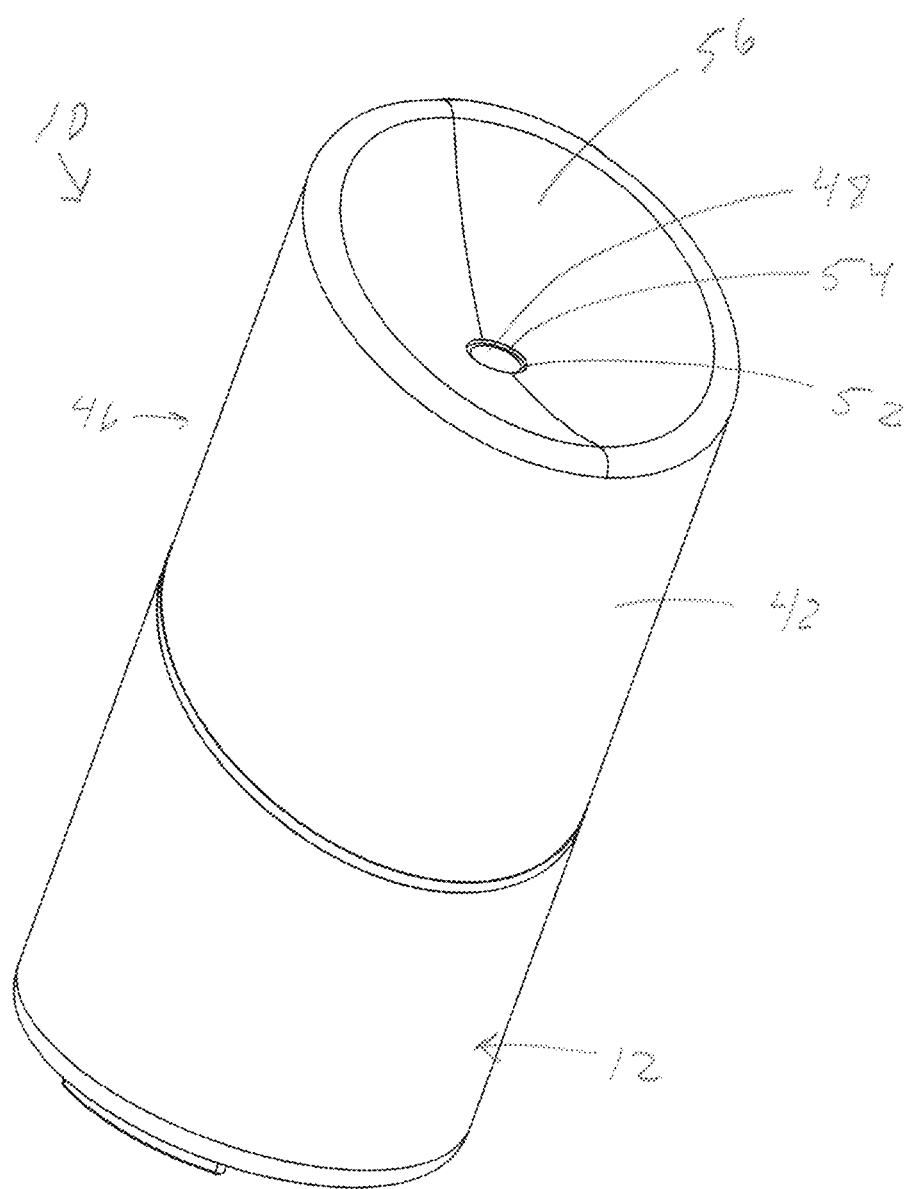

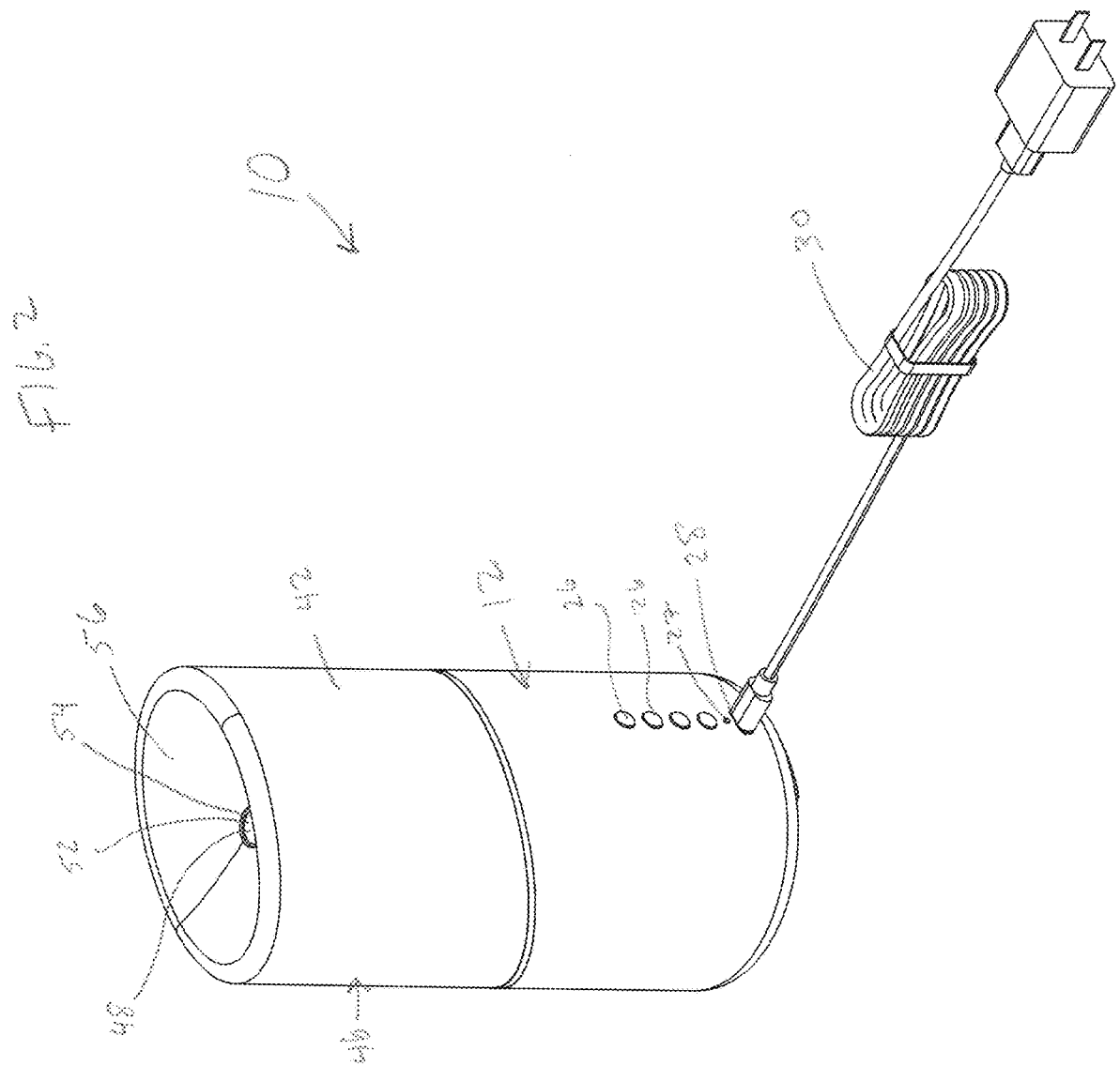

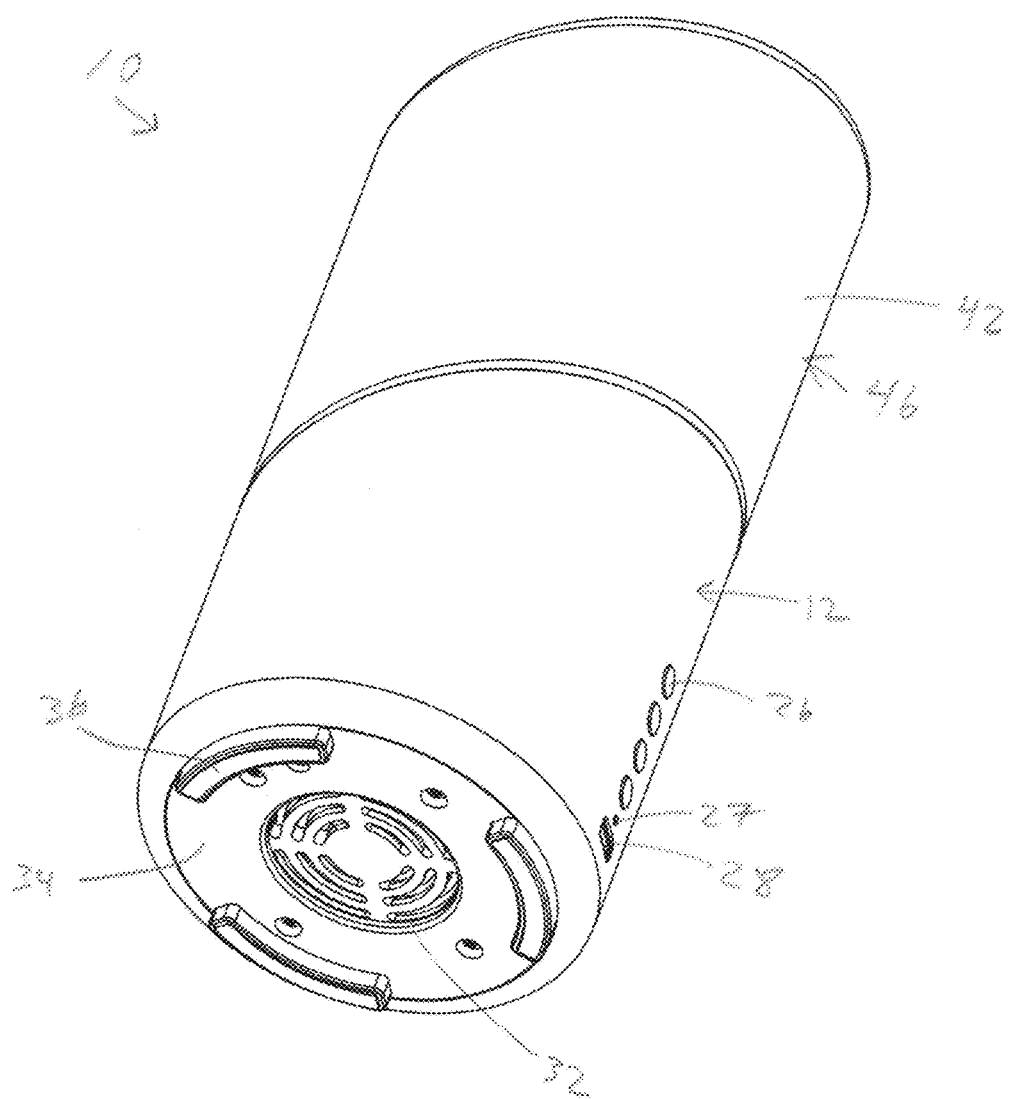

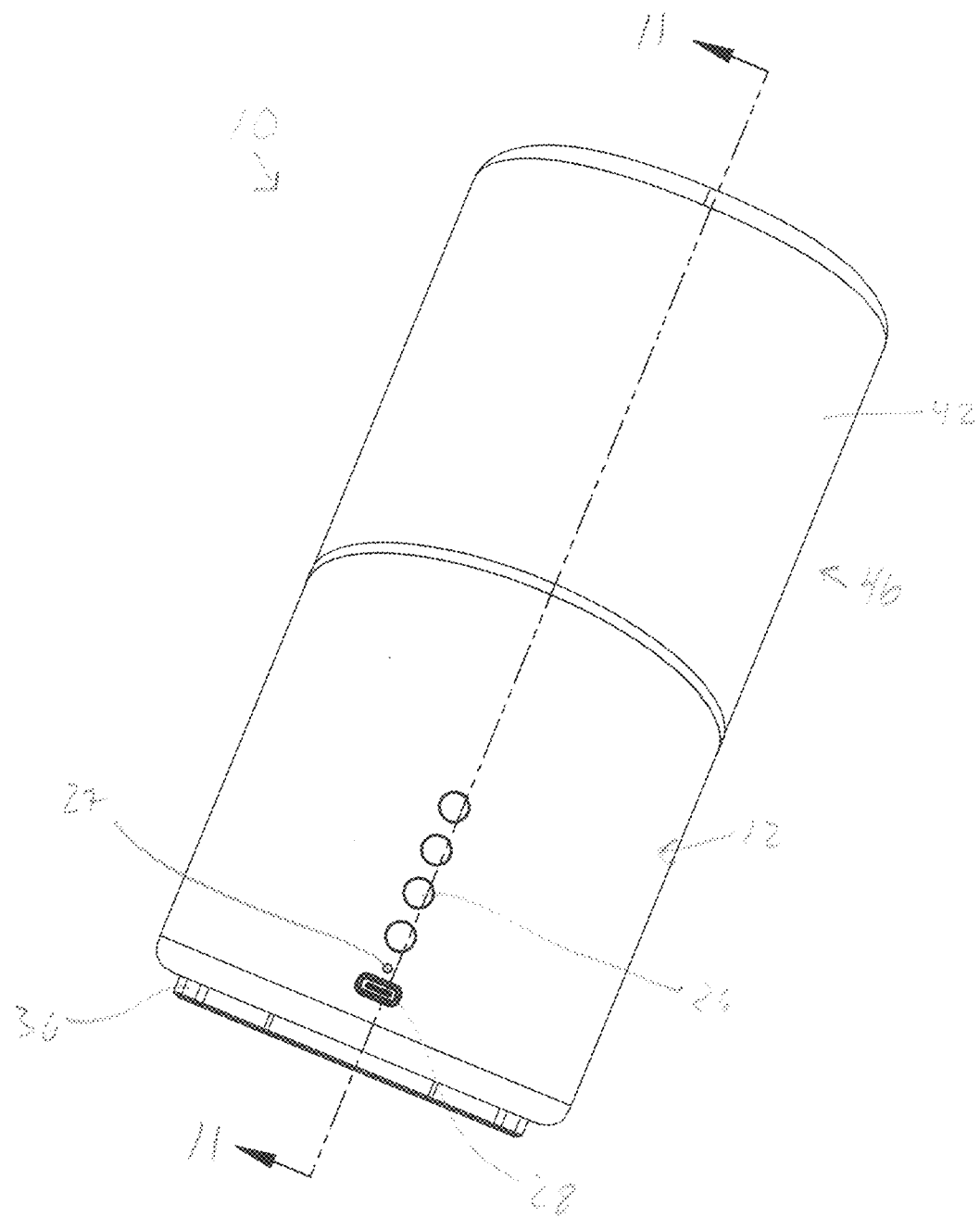

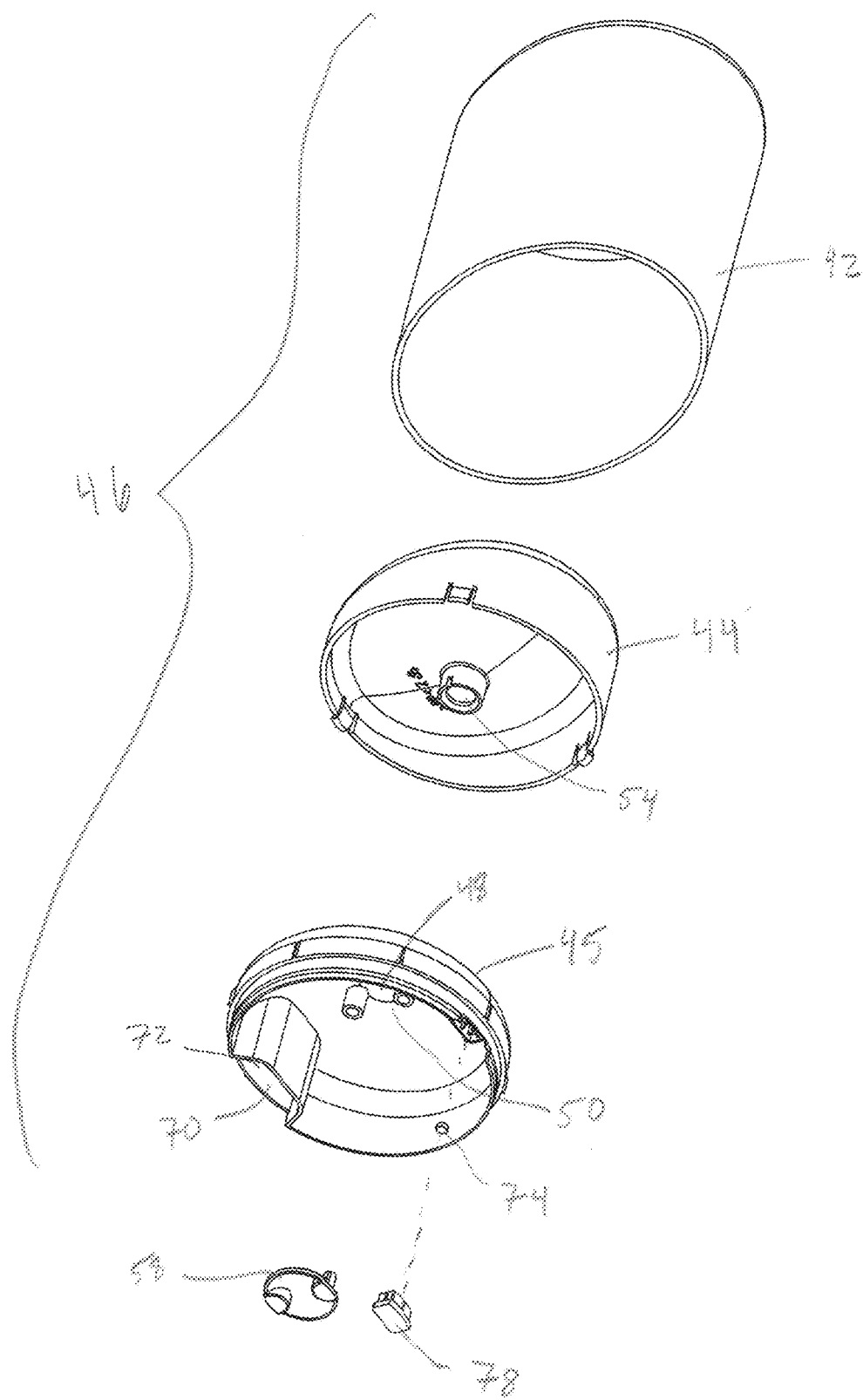

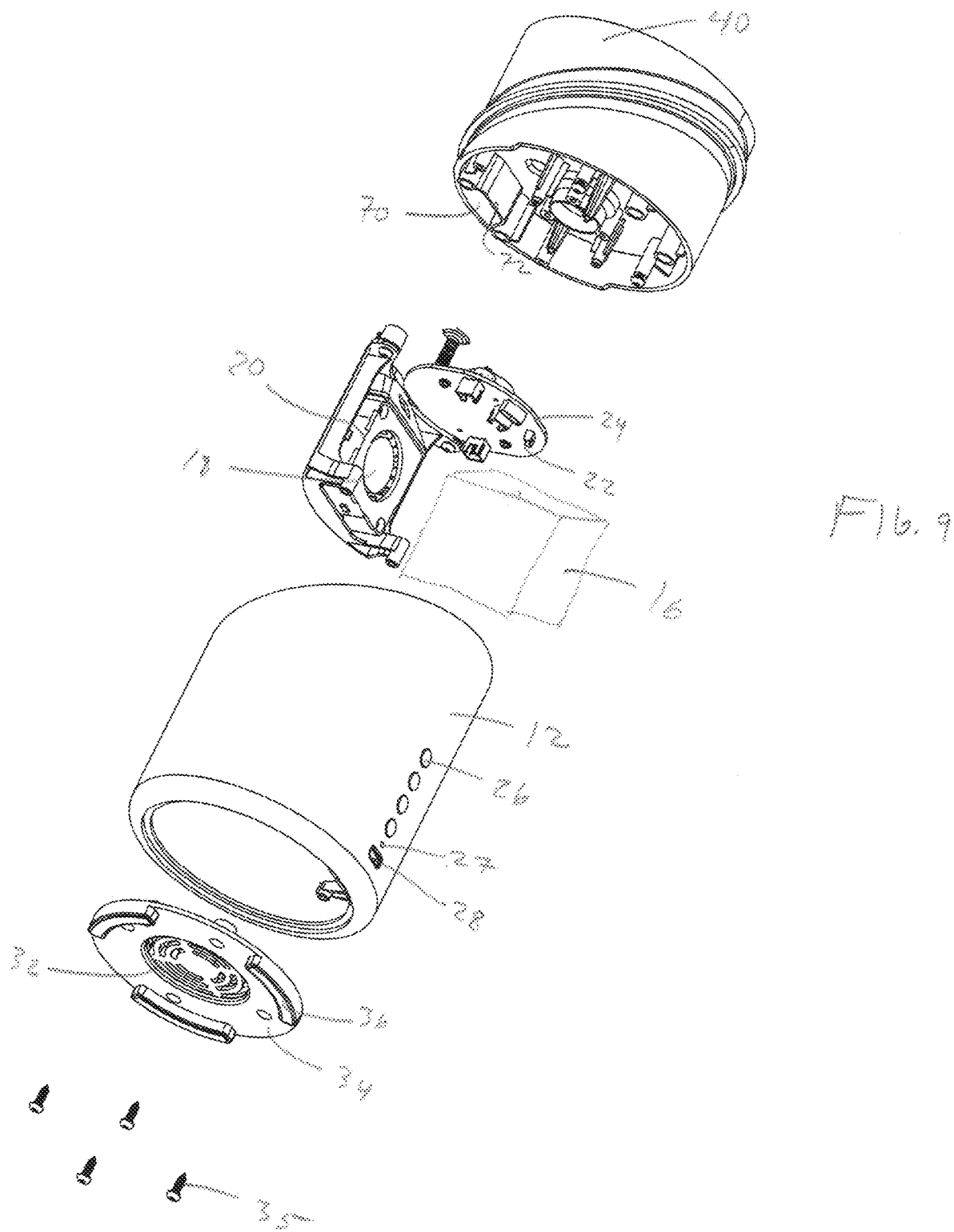

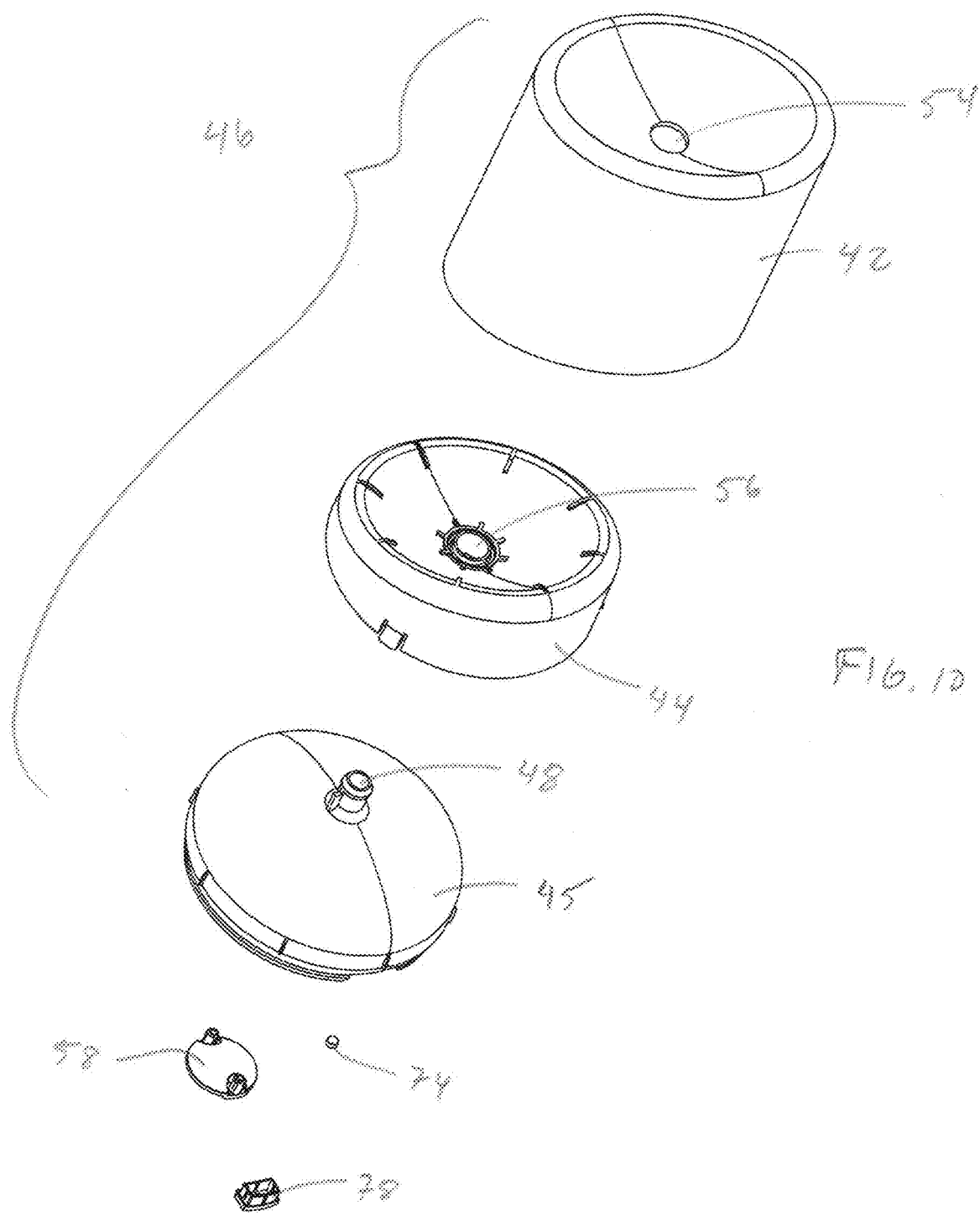

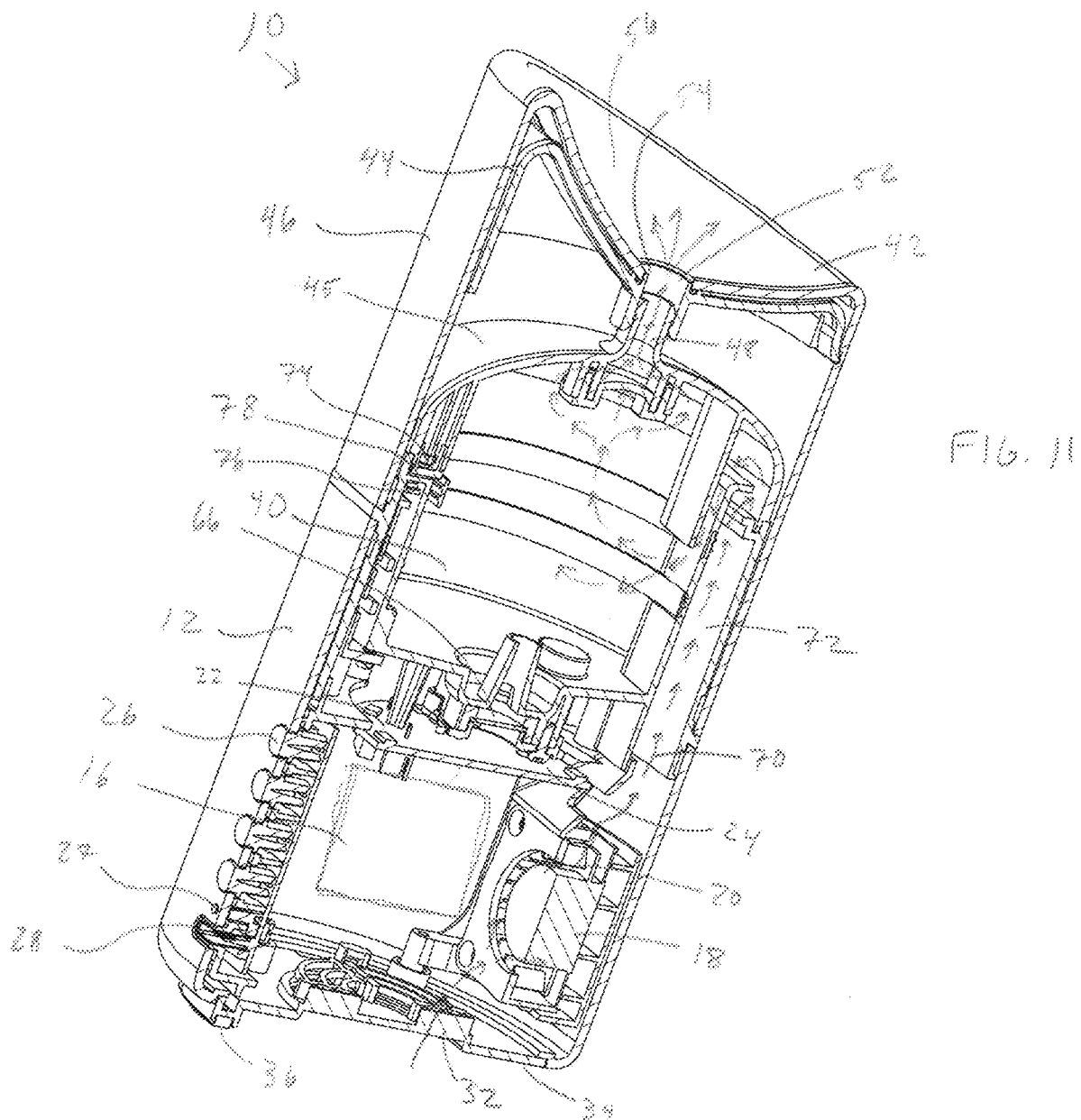

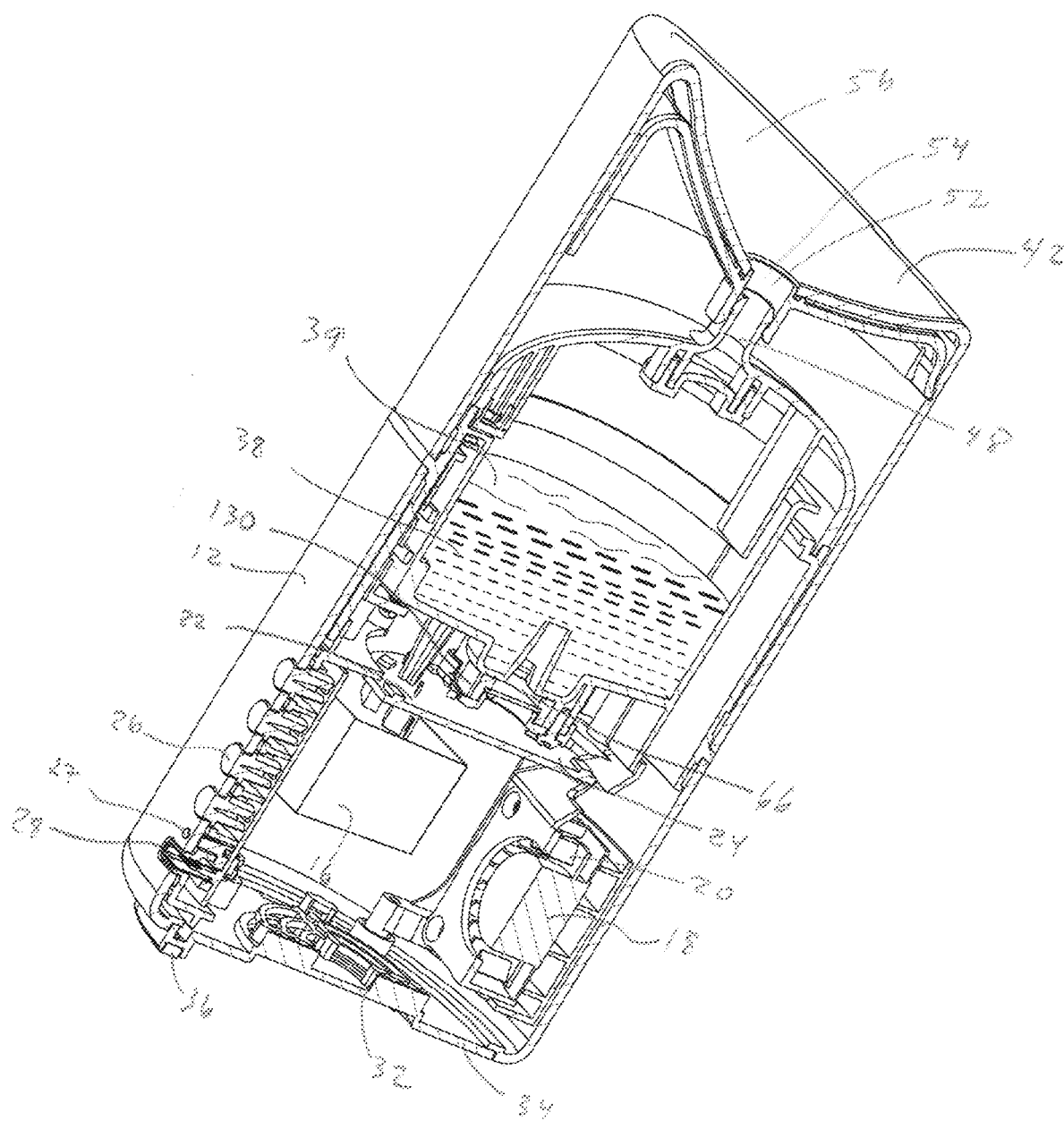

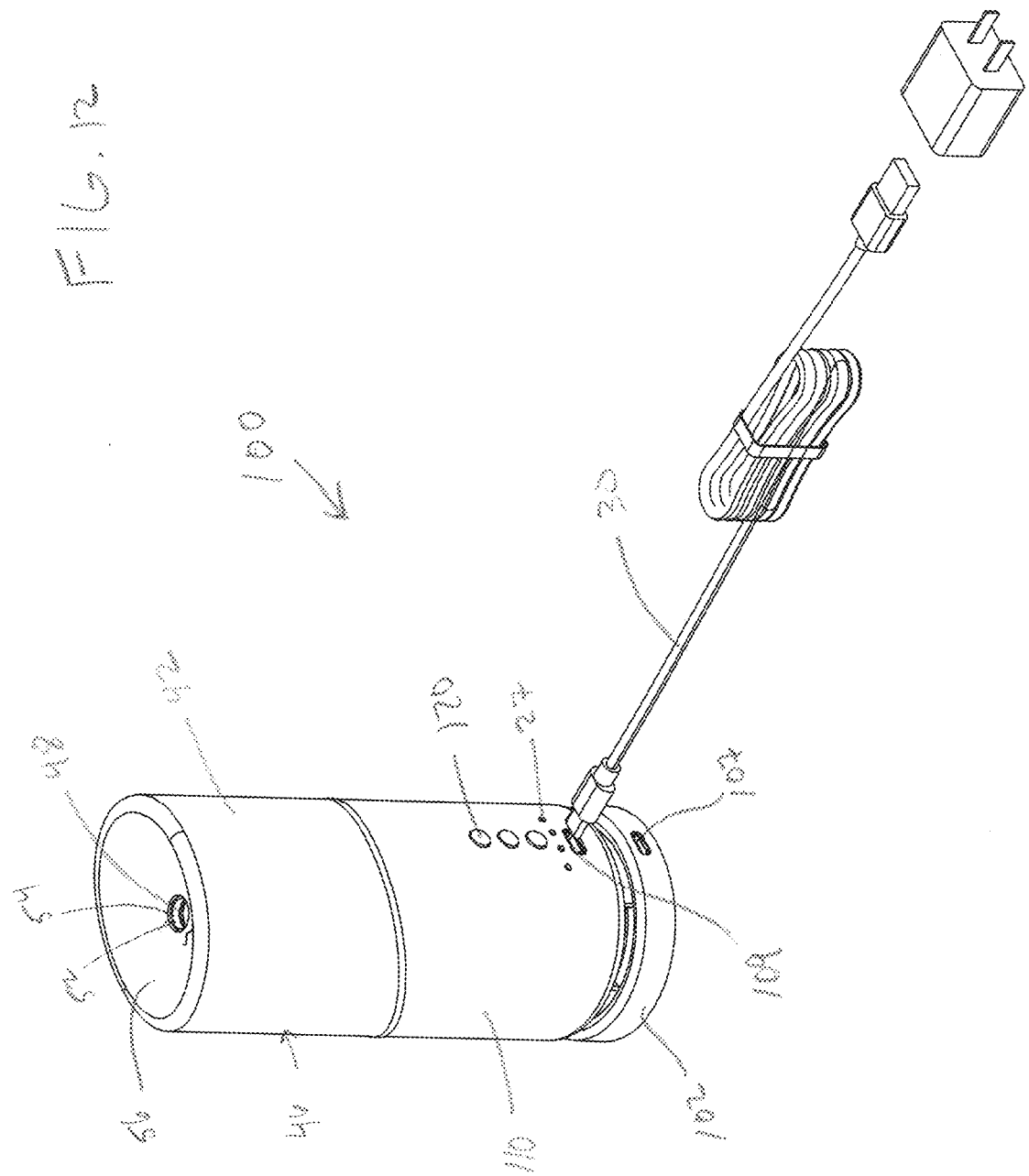

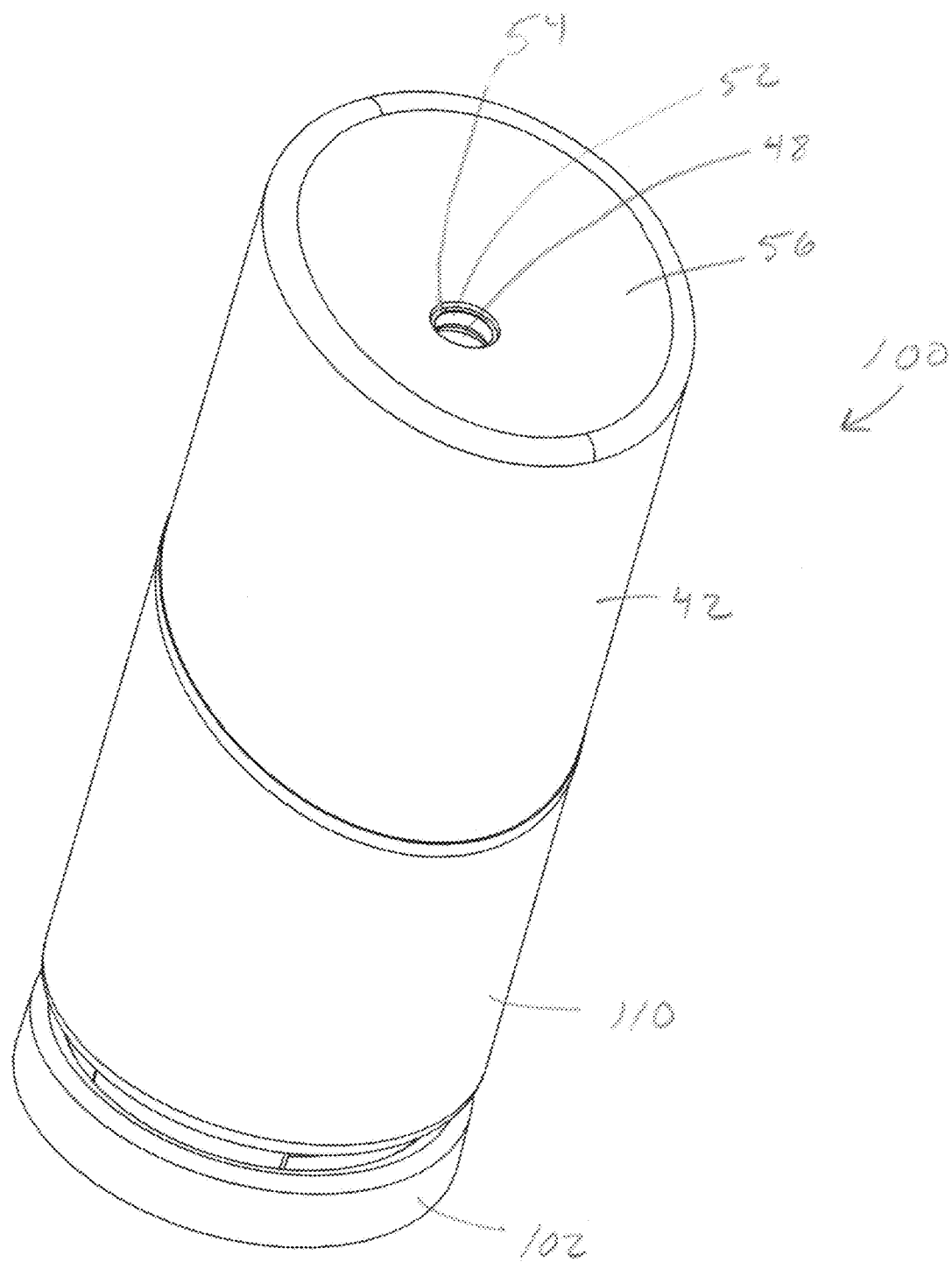

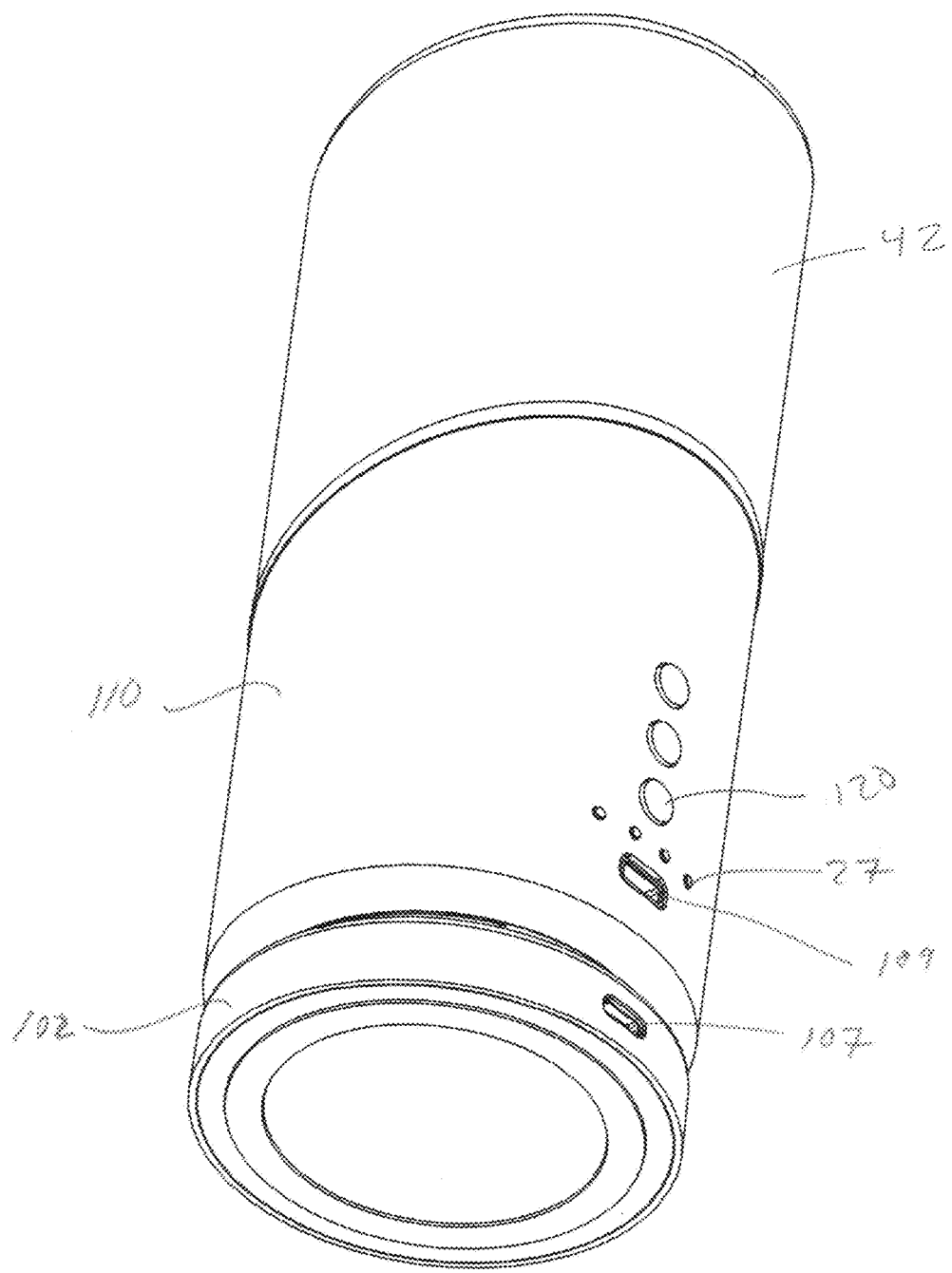

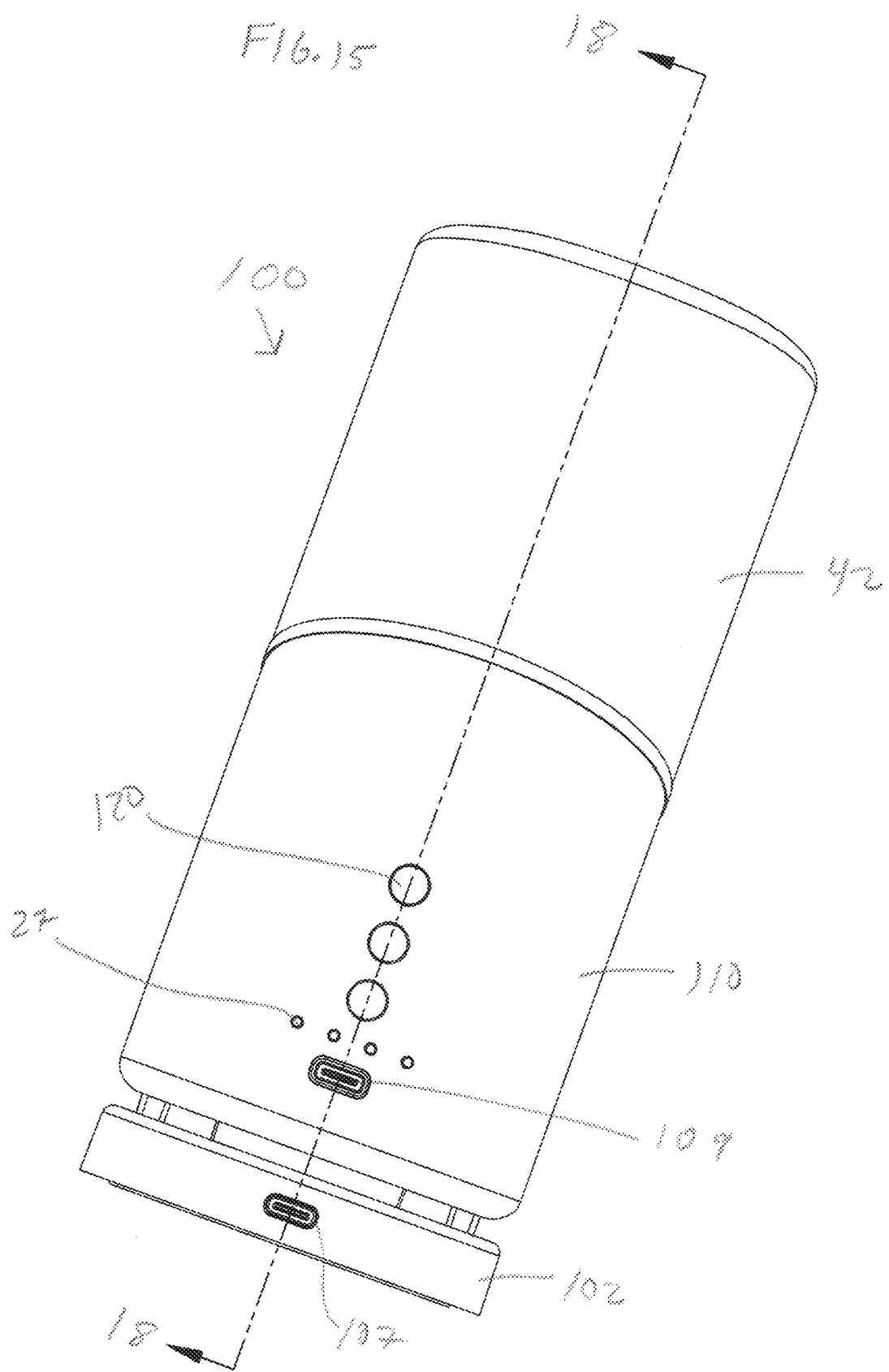

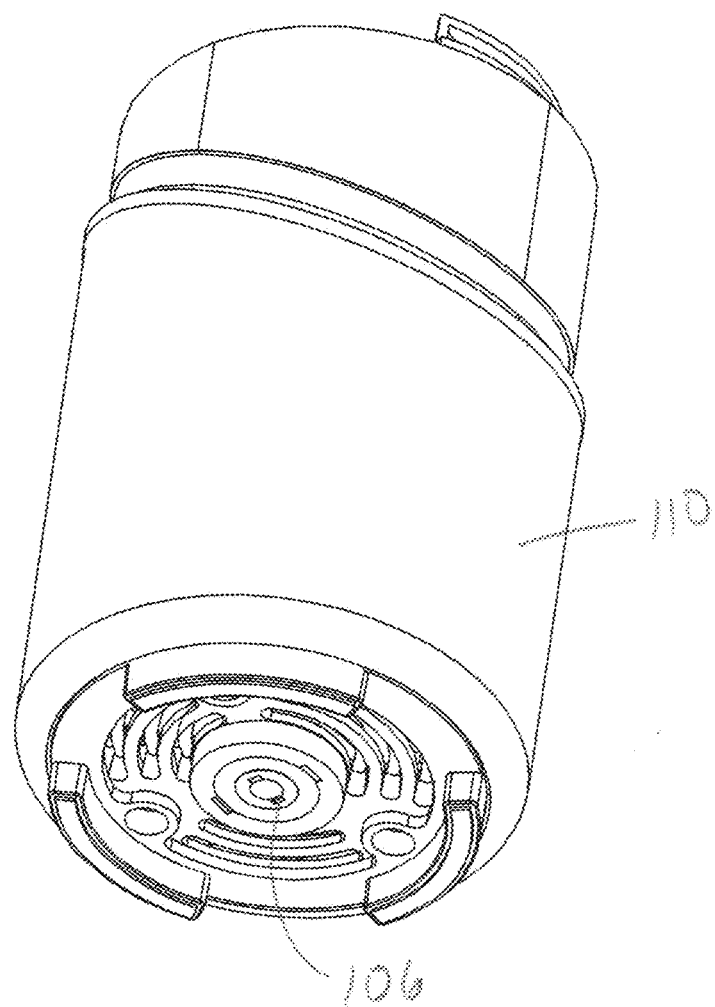

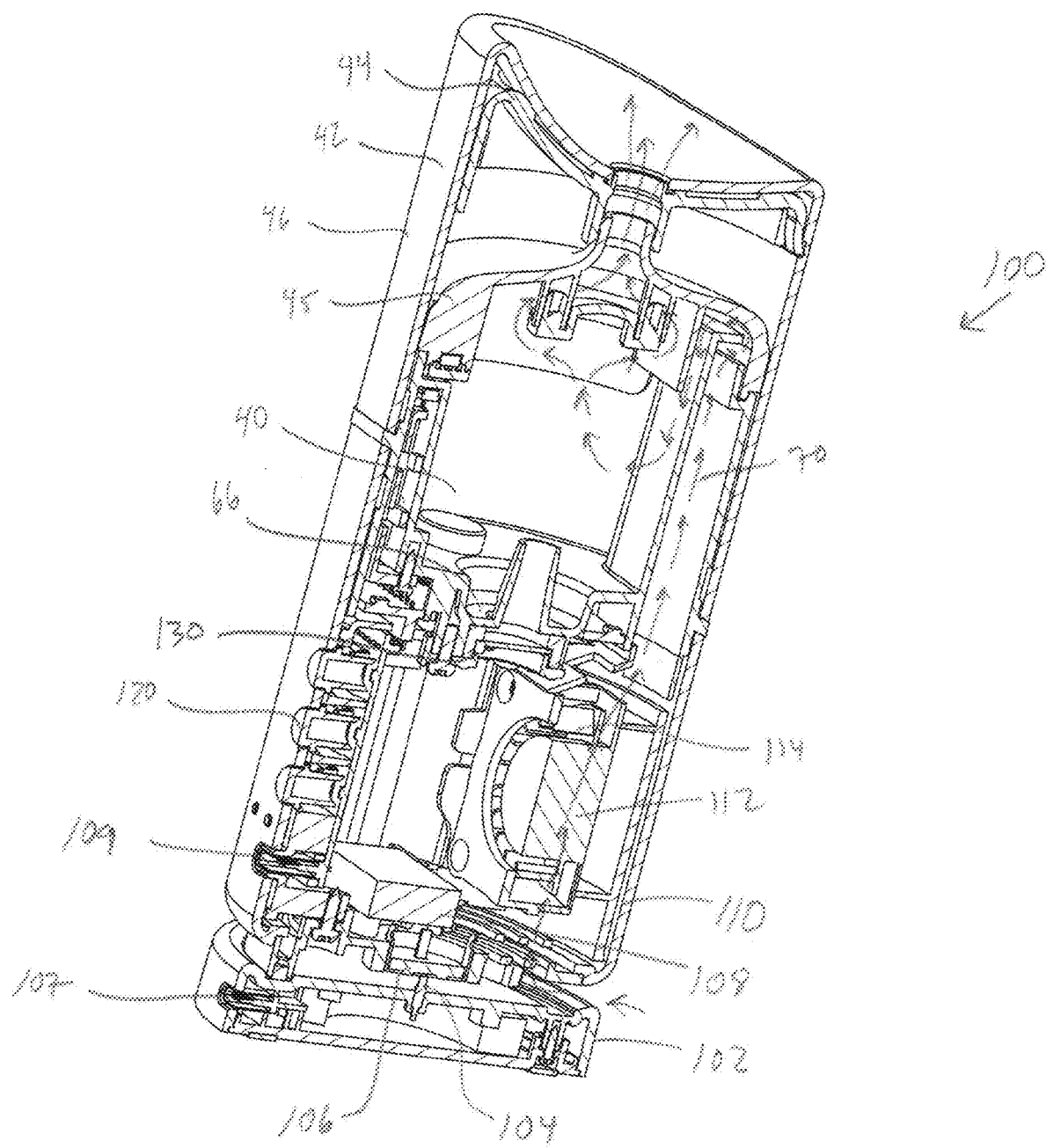

WIRELESS ULTRA SONIC DIFFUSER

BACKGROUND

Ultrasonic diffusers are becoming increasingly popular ways to disperse essential oils in homes, offices, and other spaces. Ultrasonic diffusers disperse essential oils into the air by carrying droplets of oil in water vapor. Ultrasonic diffusers typically include a liquid reservoir that has an open top to allow vapor to escape when the liquid is excited by an ultrasonic disc. It is desired to make an ultrasonic diffuser with improved liquid management to protect electrical components contained in the diffuser.

SUMMARY

The present disclosure is directed generally to ultrasonic diffusers. In particular, the disclosure relates to an ultrasonic diffuser for diffusing essential oils into a space. The diffuser includes a base defining an enclosure that may contain a rechargeable battery pack including at least one lithium-ion battery cell. A controller and a fan attached to a motor are also contained in the base. The motor turns the fan, which draws ambient air into an inlet and expels air into a diffusion path. A reservoir for holding liquid is attached to the base and positioned above the battery pack. A dome-shaped top cover is removably attached to the reservoir such that when it is attached it is positioned above the reservoir. The dome-shaped top cover includes an outlet and forms a cavity above the liquid reservoir when the top cover is attached to the reservoir. The dome-shaped top cover also has an apex and an outlet at the apex that allows vapor to escape from the cavity.

An outer casing is attached to the top cover. The outer casing has a concave upper contour and includes a hole that is aligned with the outlet to allow vapor to escape from the diffuser. In certain embodiments, the concave upper contour at least partially shields the outlet from ambient air currents.

An ultrasonic agitator is disposed in the reservoir and is controlled by at least one switch positioned on the exterior of the diffuser. The controller is electrically connected to the switch, the motor, and the ultrasonic agitator, and controls the operation of the motor.

In certain embodiments, the ultrasonic diffuser includes an internal liquid management system to direct liquid that may spill out of the reservoir away from sensitive electronic components.

BRIEF DESCRIPTION OF THE DRAWINGS

FIG. 1 is a perspective view of one embodiment of an ultrasonic diffuser in accordance with the principles of this disclosure; and FIG. 2 is another perspective view of the ultrasonic diffuser of FIG. 1, showing control switches and further showing an electric charging cable attached to the diffuser;

FIG. 3 is another perspective view of the ultrasonic diffuser of FIG. 1, showing the bottom of the diffuser;

FIG. 4 is a rear view of the ultrasonic diffuser of FIG. 1;

FIG. 7 is an exploded perspective view of a top cover for the ultrasonic diffuser of FIG. 1;

FIG. 9 is another exploded perspective view of the base of FIG. 5;

FIG. 10 is an exploded perspective view of the top cover of FIG. 7;

FIG. 11 is a section view of the ultrasonic diffuser of FIG. 1 taken generally along the line 11-11 in FIG. 4, showing a diffusion path;

FIG. 11A is another section view of the ultrasonic diffuser of FIG. 1 taken generally along the line 11-11 in FIG. 4, showing liquid in the reservoir;

FIG. 12 is a perspective view of one embodiment of an ultrasonic diffuser in accordance with the principles of this disclosure;

FIG. 13 is another perspective view of the ultrasonic diffuser of FIG. 12;

FIG. 14 is another perspective view of the ultrasonic diffuser of FIG. 12;

FIG. 15 is a rear view of the ultrasonic diffuser of FIG. 12;

FIG. 17 is a perspective view of a base for the ultrasonic diffuser of FIG. 12 showing a wireless charging port positioned on the bottom of the base; and FIG. 18 is a section view of ultrasonic diffuser of FIG. 12, taken generally along the line 18-18 in FIG. 15, showing a diffusion path.

DETAILED DESCRIPTION

Figure 6:
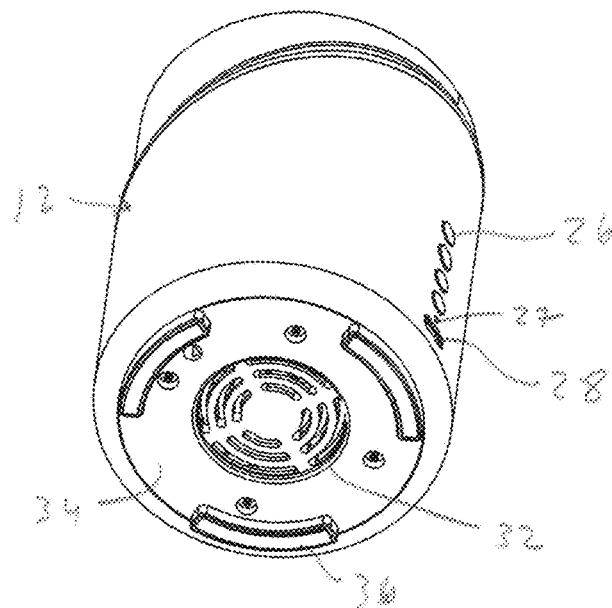
FIG. 6 is another perspective view of the base of FIG. 5, showing the bottom of the base.

Turning now to FIGS. 1-11, one embodiment of an ultrasonic diffuser 10 for dispersing vapor, typically infused with essential oil droplets, into a space is shown.

Ultrasonic diffuser 10 includes a base 12 that defines an enclosure 14 that contains all of the diffuser's electronic components. As shown, base 12 is generally cylindrical, but may be any suitable shape without departing from the principles of this disclosure. An optional rechargeable battery pack 16 may be disposed within base 12 that is electrically connected to and provides power to a motor 18 that, in turn, is attached to a fan 20. As shown, optional battery pack 16 is a lithium-ion battery pack including at least one battery cell, but any other suitable battery may alternatively be used without departing from the principles of this disclosure. In certain embodiments, ultrasonic diffuser 10 may omit battery pack 16, obtaining power from an electrical outlet.

In the embodiment shown, battery pack 16 is also electrically connected to and provides power to a controller 22. In the embodiment shown, controller 22 is contained on a printed circuit board 24 and controls operation of the diffuser, which is described in greater detail below. In certain embodiments, the controller 22 may be split into multiple circuit boards without departing from the principles of this disclosure. The controller 22 is also electrically attached to switches 26 that can be used to control operation of the diffuser 10. In the embodiment shown, a status light 27 and charge port 28 are positioned below the switches 26. An electric charging cable 30 may be removably attached to charge port 28 to charge the battery pack 16 and can also power the diffuser 10, if desired.

As shown in FIG. 3, base 12 includes an air inlet 32. In the embodiment shown, the air inlet 32 is integrally formed in the bottom cover 34 of base 12, but it may be positioned in any suitable location and may or may not be integrally formed with the bottom cover or base without departing from the principles of this disclosure. Bottom cover 34 is attached to base 12 by a plurality of screws 35. Any suitable fastener may alternatively be used to attach bottom cover 34 to base 12. In the embodiment shown, base 12 includes a plurality of feet 36 that raise bottom cover 34 off of a surface on which diffuser 10 is set. Raising bottom cover 34 off of a surface provides a path for ambient air to enter base 12 through the air inlet 32. As shown in FIG. 11, ambient air is drawn into air inlet 32 by negative air pressure inside base 12 generated by actuation of fan 20.

As shown in FIG. 11, a reservoir 40 is attached to base 12. In the embodiment shown, reservoir 40 is attached to base 12 above the enclosure 14 and may be filled with liquid 38, typically a combination of water and essential oils.

Diffuser 10 includes an outer casing 42, which is removably attached to base 12. As shown in FIGS. 7 and 10, a support ring 44 is attached to the inside of outer casing 42. Support ring 44 is, in turn, attached to a dome shaped reservoir lid 45. Combined, outer casing 42, support ring 44, and reservoir lid 45 form a top cover 46 that may be removably attached to base 12. Reservoir lid 45 further includes an outlet 48 positioned at the apex 50 of the dome shaped lid. Outlet 48 is in fluid communication with the reservoir 40 provides a path to allow vapor to escape from air cavity 62. Similarly, outer casing 42 and support ring 44 include holes 52, 54 that align with outlet 48 when top cover 46 is assembled.

Top cover 46 further includes a magnet 74 positioned such that when the top cover is attached to base 12, the magnet interacts with a sensor 76 disposed in the base. In the embodiment shown, a magnet cover 78 separates magnet 74 from the interior of top cover 46, but any suitable means of attaching magnet 74 to top cover may be used without departing from the principles of this disclosure. Sensor 76 determines whether top cover 46 is installed on the base 12. Whenever top cover 46 is not installed on the base 12, sensor 76 sends a signal to controller 22 that the top cover is not present and disables the ultrasonic agitator 66. Although a magnetic sensor 76 is used in the embodiment shown, any other suitable sensor may be used without departing from the principles of this disclosure.

In the embodiment shown, outer casing 42 is generally cylindrical in cross-section and includes a top 56 that has a concave profile leading down to outlet 48. The concave profile of top 56 provides at least partially shields outlet 48 from ambient air currents that may disturb the flow of vapor as it passes through outlet 48. In addition, although unlikely, the concave profile of top 56 provides a basin that can catch any droplets that may escape the outlet but are too large to be diffused into the air and direct the droplets back into reservoir 40. It is unlikely that larger than desired droplets would escape outlet 48, however, because a water plate 58 is attached near the apex 50 of reservoir lid 45, but offset vertically from the apex, such that the vapor does not have a direct path up through outlet 48. Rather, the vapor must pass around water plate 58, through a gap 60 between the water plate, apex 50, and outlet 48.

Figure 5:
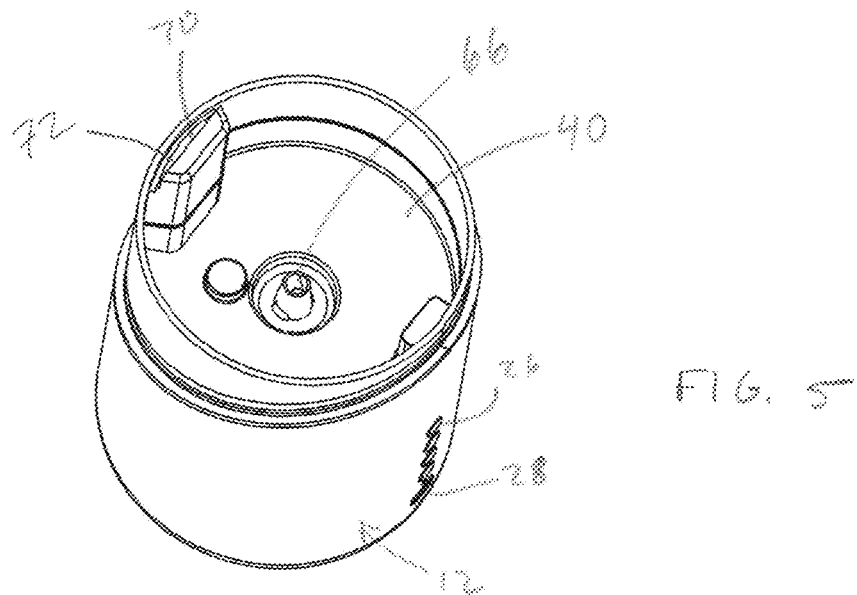
FIG. 5 is a perspective view of a base for the ultrasonic diffuser of FIG. 1, showing a liquid reservoir.
Figure 8:
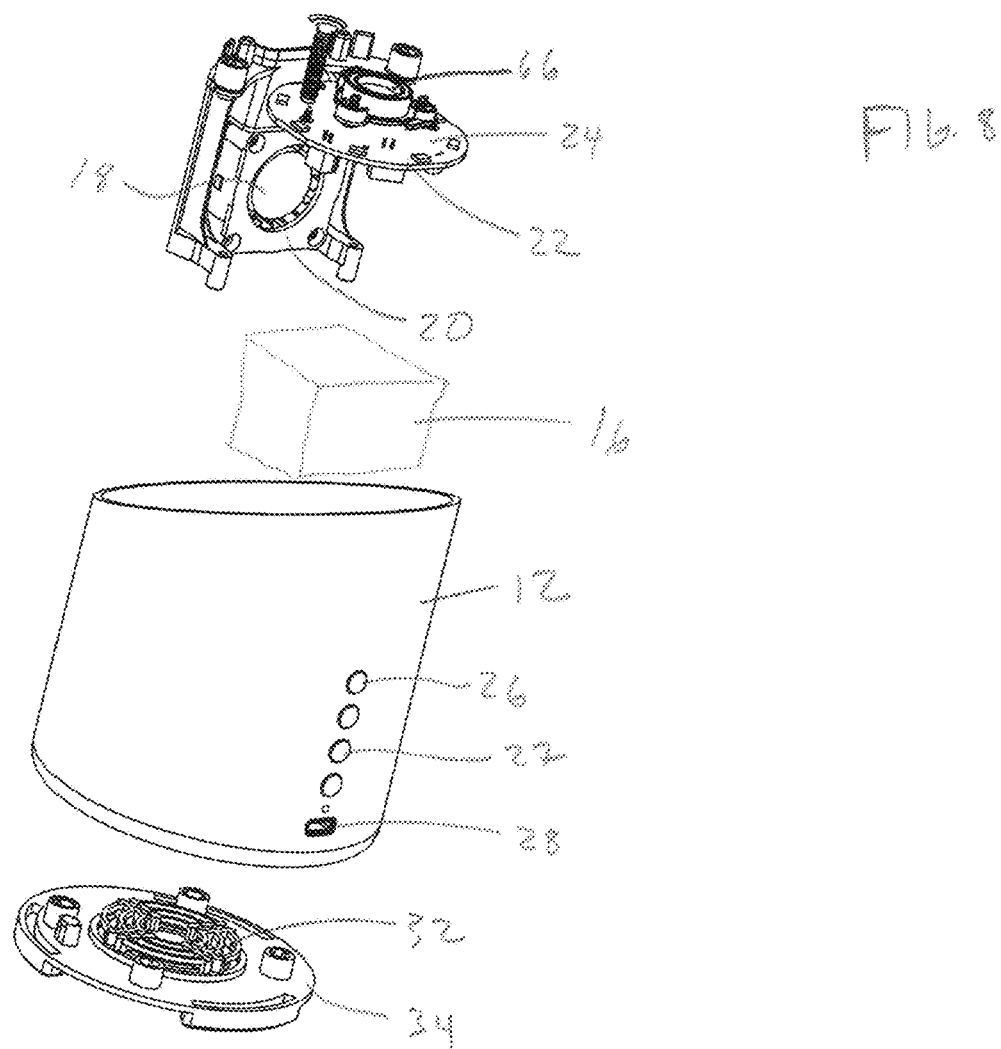
FIG. 8 is an exploded perspective view of the base of FIG. 5.
Figure 16:
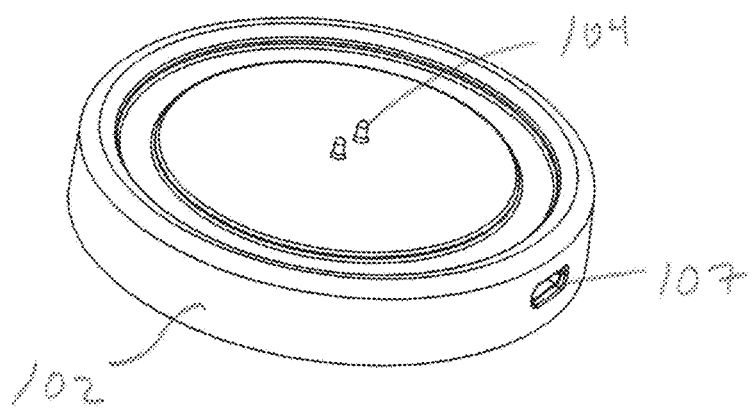
FIG. 16 is a perspective view of a wireless charging base for ultrasonic diffuser of FIG. 12.

As shown in FIG. 5, an ultrasonic agitator 66 is positioned at the bottom of reservoir 40. In the embodiment shown, ultrasonic agitator 66 is a disc or membrane style agitator, but any suitable agitator may alternatively be used. The ultrasonic agitator 66 is electrically attached to controller 22. When activated, ultrasonic agitator 66 vibrates to agitate any liquid 38 in the reservoir 40 such that the liquid is separated into very small particles. In the embodiment shown, the reservoir may be filled with water and essential oil. When the water particles are separated, they become negatively charged and are light enough to be dispersed into an air cavity 62 above the liquid level 39. Essential oil micro-droplets are released into the air with the negatively charged water particles. Air drawn into inlet 32 by fan 20 passes through the fan and is expelled into a diffusion path 70 that travels through a passageway 72 within the enclosure 14 and is in fluid communication with air cavity 62. As air exits passageway 72, it is directed into air cavity 62, picking up vapor and oil micro droplets and guiding them to outlet 68, where the air, vapor and oil droplets are expelled into the space outside the diffuser 10.

Turning now to FIGS. 12-18, an alternative embodiment of an ultrasonic diffuser 100 is shown. Ultrasonic diffuser 100 is virtually identical to the embodiment previously described, except this embodiment includes a wireless charging base 102. Wireless charging base 102 includes a charging post 104 that interacts with a charging port 106 on the bottom of ultrasonic diffuser 100. Charging port 106 is electrically connected to the controller 116 and battery pack 108. Wireless charging base 102 also includes a wired charge port 107 to provide power to the charging base.

As shown, ultrasonic diffuser 100 also includes a wired charge port 109 that can be used with electric charging cable 30 when wireless charging base 102 is unavailable. When a user sets ultrasonic diffuser 100 on wireless charging base 102, an electrical connection is made between charging posts 104 and charging port 106 and electrical current can flow to rechargeable battery pack 108. Of course, any other suitable means of providing wireless charging including, but not limited to magnetic induction, may be used without departing from the principles of this disclosure. As shown, ultrasonic diffuser 100 includes a base 110. As in the previous embodiment, base 110 is generally cylindrical, but may be any suitable shape without departing from the principles of this disclosure.

Rechargeable battery pack 108 is disposed within base 110 and is electrically connected to and provides power to a motor 112 that, in turn, is attached to a fan 114. Battery pack 108 is also electrically connected to and provides power to a controller 116. In the embodiment shown, controller 116 is contained on a printed circuit board 118 and controls operation of the diffuser 100, which is described in greater detail below. In certain embodiments, the controller 116 may be split into multiple circuit boards without departing from the principles of this disclosure. The controller 116 is also electrically attached to switches 120 that can be used to control operation of the diffuser 100. The components positioned above base 110 in the embodiment shown are identical to the embodiment previously described.

Returning to FIGS. 11 and 18, ultrasonic diffusers 10, 100 each include a liquid management system 130 provides a path for liquid 38 that diverts any liquid that leaks out of reservoir 40 away from sensitive electronic components such as controller 22, 116, switches 26, 120, and motor 18, 112. Liquid management system 130 protects the aforementioned electronic components in the event a user moves ultrasonic diffusers 10, 100 with liquid 38 in reservoir 40. It is likely that a user would move the diffusers 10, 100 when they are battery-powered and much more portable than a diffuser that is tied to an electrical outlet.

Although the embodiments as herein described are what is perceived to be the most practical and preferred embodiments, this disclosure is not intended to be limited to the specific embodiments set forth above. Rather, modifications may be made by one of skill in the art of without departing from the spirit or intent of the principles of this disclosure.

What is claimed is:

1. An ultrasonic diffuser comprising:
a base defining an enclosure;

a fan disposed within the base, the fan attached to a motor, wherein the motor turns the fan, which moves ambient air into an inlet and out to a diffusion path;

a reservoir for holding a liquid, the reservoir attached to the base;

a dome-shaped top cover positioned above the reservoir, wherein the top cover is removably directly attached to the reservoir;

the dome-shaped top cover including an outlet and providing an air cavity above the reservoir when the top cover is attached to the reservoir;

the dome-shaped top cover having an apex including the outlet that allows a vapor to escape from the air cavity;

an outer casing attached to the top cover, the outer casing having a concave upper contour leading down to the outlet and including a hole aligned with the outlet to allow the vapor to escape from the diffuser, wherein the concave upper contour at least partially shields the outlet from ambient air currents;

an ultrasonic agitator disposed in the reservoir;

at least one switch to control operation of the diffuser; and a controller electrically connected to the switch, the motor, and the ultrasonic agitator, the controller controlling the operation of the motor;

wherein the concave upper contour of the outer casing forms a basin capable of catching any liquid droplets that may escape the reservoir through the outlet and returning the liquid droplets to the reservoir through the outlet.

2. The ultrasonic diffuser of claim 1, further including a rechargeable battery pack including at least one lithium-ion battery cell, the rechargeable battery pack disposed within the base.

3. The ultrasonic diffuser of claim 1, further including a magnetic sensor disposed in the base and a magnet disposed in the top cover, such that the magnetic sensor senses when the top cover is installed on the base.

4. The ultrasonic diffuser of claim 1, wherein the diffusion path is in fluid communication with the fan, air cavity, and the outlet.

5. The ultrasonic diffuser of claim 2, further including a wireless charging base, the wireless charging base including a charging post.

6. The ultrasonic diffuser of claim 5, further including a charging port that selectively attaches electrically to the charging post.

7. The ultrasonic diffuser of claim 1, further including a support ring disposed between the dome shaped top cover and the outer casing.

8. The ultrasonic diffuser of claim 1, further including a water plate offset from the outlet, the water plate preventing large water droplets from passing through the outlet.

9. A method of using an ultrasonic diffuser comprising the steps of:

providing an ultrasonic diffuser including a base defining an enclosure, a fan disposed within the base, the fan attached to a motor, wherein the motor turns the fan, which moves ambient air into an inlet and out to a diffusion path, a reservoir for holding liquid, the reservoir attached to the base, a dome-shaped top cover positioned above the reservoir, wherein the top cover is removably directly attached to the reservoir, the dome-shaped top cover including an outlet and providing an air cavity above the reservoir when the top cover is attached to the reservoir, the dome-shaped top cover having an apex including the outlet that allows a vapor to escape from the air cavity, an outer casing attached to the top cover, the outer casing having a concave upper contour leading down to the outlet, forming a basin, and including a hole aligned with the outlet to allow the vapor to escape from the diffuser, wherein the concave upper contour at least partially shields the outlet from ambient air currents, an ultrasonic agitator disposed in the reservoir, at least one switch to control operation of the diffuser, and a controller electrically connected to the at least one switch, the motor, and the ultrasonic agitator, the controller controlling the operation of the motor;

temporarily removing the top cover from the reservoir;

filling the reservoir with liquid;

reattaching the top cover to the base;

providing electricity to the controller;

activating the fan and ultrasonic agitator by pressing the at least one switch, the agitator converting the liquid to the vapor, the fan drawing ambient air into the base, along a diffusion path through the air cavity;

forcing the vapor through the outlet and into a space surrounding the diffuser;

catching any liquid droplets that escape through the outlet with the outer casing; and returning the liquid droplets to the reservoir through the outlet.

10. The method of using an ultrasonic diffuser of claim 9, further including the step of adding an essential oil to the liquid.

11. The method of using an ultrasonic diffuser of claim 9, wherein the diffusion path is in fluid communication with the fan, air cavity, and the outlet.

12. The method of using an ultrasonic diffuser of claim 9, wherein the diffuser includes a rechargeable lithium-ion battery pack.

13. The method of using an ultrasonic diffuser of claim 12, further including the steps of:

charging the lithium-ion battery pack;

removing the diffuser from an exterior electric power source; and operating the diffuser using only electricity provided by the lithium-ion battery pack.

\* \* \* \* \*